(12) United States Patent
Lee et al.

(10) Patent No.: US 6,254,637 B1
(45) Date of Patent: Jul. 3, 2001

(54) ARTIFICIAL CORNEA AND IMPLANTATION THEREOF

(75) Inventors: Jin Hak Lee, Seongnam; Won Ryang Wee; Moo Suk Lee, both of Seoul, all of (KR)

(73) Assignee: Lucid Korea Co., Ltd., Seoul (KR)

( * ) Notice: Subject to any disclaimer, the term of this patent is extended or adjusted under 35 U.S.C. 154(b) by 0 days.

(21) Appl. No.: 09/546,329

(22) Filed: Apr. 10, 2000

(51) Int. Cl.$^7$ ........................................................ A61F 2/14
(52) U.S. Cl. ........................ 623/5.14; 623/5.4; 128/898
(58) Field of Search ............................... 623/5.11, 5.14; 128/898

(56) References Cited

U.S. PATENT DOCUMENTS

| | | | |
|---|---|---|---|
| 3,458,870 | * | 8/1969 | Stone, Jr. ........................ 623/5.11 |
| 4,470,159 | * | 9/1984 | Peyman ........................... 623/5.11 |
| 5,489,301 | * | 2/1996 | Barber ............................ 623/5.11 |
| 5,843,185 | * | 12/1998 | Leon et al. ..................... 623/5.11 |

* cited by examiner

*Primary Examiner*—Dinh X. Nguyen
(74) *Attorney, Agent, or Firm*—Jones, Tullar & Cooper, P.C.

(57) ABSTRACT

An artificial cornea capable of preventing a separation thereof from an eyeball of the patient during an implant operation thereof while avoiding post-operative complications at the interface between the artificial cornea and the patient's cornea, such as erosive tissue necrosis (melting), leakage of aqueous humor, infection, extrusion of the implant, and intraocular inflammation. The artificial cornea includes an artificial cornea body having, at a lower portion thereof, a cylindrical portion adapted to be arranged in the interior of a patient's eyeball, and, at an upper portion thereof, an optical portion adapted to be exposed through an anterior portion of the patient's eyeball, the optical portion having a diameter less than that of the cylindrical portion to define a step at a lower end thereof, a skirt fitted around the optical portion of the cornea body and seated on the step, an anterior flange coupled to an upper surface of the skirt, and a support member attached to a lower end of the cylindrical portion and adapted to support the artificial cornea body. An amnion is covered on the implant in order to promote a stable graft of the artificial cornea to the patient's cornea during an initial reaction period for the recovery of a cut portion of the patient's cornea.

3 Claims, 2 Drawing Sheets

ARTIFICIAL CORNEA AND IMPLANTATION THEREOF

BACKGROUND OF THE INVENTION

1. Field of the Invention

The present invention relates in general to an artificial cornea and an implantation thereof. More particularly, the present invention relates to an artificial cornea capable of preventing a separation thereof from an eyeball of the patient during an implant operation thereof while avoiding post-operative complications at the interface between the artificial cornea and the patient's cornea, such as erosive tissue necrosis (melting), leakage of aqueous humor, infection, extrusion of the implant, and intraocular inflammation.

2. Description of the Prior Art

Corneas severely scarred due to thermal or chemical burns, heavily vascularized or vesiculated corneas, or corneas of ocular pemphigoid may be progressed to dry eye syndromes such as StevensJohnson syndrome, so that they may be severely injured, thereby losing vision.

Although such injured corneas may recover vision by the transplantation of human homologous corneal tissue, the transplantation of such human homologous corneal tissue exhibits a high probability of failure. For this reason, the implantation of an artificial cornea has been highlighted.

Moreover, in the case where the transplantation of human homologous corneal tissues is basically impossible or has been repeatedly failed, the implantation of an artificial cornea ultimately becomes a unique way to recover vision.

Up to date, there have been many efforts in the research and development for materials and designs of artificial corneas. In the 1950's, cornea implant operations using an acrylic resin as an artificial cornea were proposed. In the 1960's, Cardona, who played an important role in the research of artificial corneas, developed a bolt and nut type artificial cornea, which has been used until recently.

Necessity and importance for research and development of artificial corneas are as follows:

A. Technical Aspects

In the cases of severe dry eye conditions, thermal or chemical burns of corneas, ocular pemphigoid, Stevens-Johnson syndrome, and a repeatedly failed cornea implantation, the transplantation of human homologous corneal tissues exhibits a low possibility to recover vision. In such cases, therefore, the implantation of an artificial cornea should be taken into consideration, as an ultimate method for achieving an improvement in vision. However, all artificial corneas developed up to now have many drawbacks. For this reason, the development of an artificial cornea having an approved stability and utility, has been strongly required in the world.

B. Economical and Industrial Aspects

In the case of various intractable corneas, to which a transplantation of homologous corneal tissues is impossible, the implantation of an artificial cornea is the ultimate way to recover vision. However, many countries have no ability to manufacture such an artificial cornea. For this reason, all artificial corneas available in those countries are those manufactured by and imported from advanced countries, including U.S.A. and France, having an ability to manufacture those artificial corneas. However, such artificial corneas are very expensive because they are patented products. In spite of such high costs, most of the currently available artificial corneas exhibit a limited success even after repeated implant operations, and furthermore cause various complications resulting in blindness. This increases medical expenses of individuals and nations, and also results in the high loss of labor.

C. Social and Cultural Aspects

In advanced countries, artificial corneas were researched and developed for the treatment of intractable corneas to which homologous corneal tissues could not be implanted. However, in Korea, there is another reason for the urgent development of artificial corneas. That is, donor corneas necessary for the implantation of homologous corneal tissues are in great shortage in Korea because most Korean people do not want to donate organs after death due to traditional Confucian ideas. For this reason, there are many patients who can recover vision even by the implantation of homologous corneal tissues, and maintain a normal social life. In this regard, if more stable artificial corneas are developed, it is then expected that many patients suffering from the corneal disorder can easily recover vision and return to a functional and productive role in society.

Artificial corneas developed up to now involve two main failures. One failure is a structural failure, that is, a separation of the artificial cornea from the peripheral tissue due to an instable graft of the artificial cornea to the peripheral tissue. Another failure is a functional failure caused by the fact that tissues with cicatricial pemphigoid cover the optical part of eye.

In order to overcome such failure factors of artificial corneas, the inventor has made active research for the design of artificial corneas, the surface treatment of artificial cornea components such as optical and support parts, the implant operation method, and the treatment conducted after the implant operation. By virtue of such research, the inventor could determine optimum conditions capable of providing an artificial cornea having a maximum biocompatibility and a stability. In particular, the maximum biocompatibility and stability of the artificial cornea was established, based on experiments conducted with animals. The experimental results may be used as fundamental materials for future clinical demonstrations and industrial applications in order to achieve an improvement in medical technology.

SUMMARY OF THE INVENTION

It is therefore an object of the present invention to overcome the above mentioned failure factors, and to provide an artificial cornea exhibiting a maximum biocompatibility and a high stability, along with an effective implantation method for the artificial cornea.

In accordance with one aspect, the present invention provides an artificial cornea comprising: an artificial cornea body having, at a lower portion thereof, a cylindrical portion adapted to be arranged in the interior of a patient's eyeball, and, at an upper portion thereof, an optical portion adapted to be exposed through an anterior portion of the patient's eyeball, the optical portion having a diameter less than that of the cylindrical portion to define a step at a lower end thereof; a skirt fitted around the optical portion of the cornea body and seated on the step; an anterior flange coupled to an upper surface of the skirt; and a support member attached to a lower end of the cylindrical portion and adapted to support the artificial cornea body.

In accordance with another aspect, the present invention provides a method for implanting the above mentioned artificial cornea to a cornea of a patient's eye, comprising the steps of: preparing a human amnion, and maintaining the prepared human amnion in an antibiotic state; subjecting the patient's cornea to a 360 conjunctival incision; suturing a Flieringa fixation ring at four positions to the sclera exposed through the incised conjunctiva, thereby fixing the Flieringa fixation ring to the sclera; peeling off the epithelium of the patient's cornea; conducting a partial trephination for the resultant patient's cornea, thereby forming, in the patient's cornea, a central orifice having a depth corresponding to about ½ to ⅓ of the thickness of the patient's cornea; subjecting the resultant patient's cornea to a 360 intralamellar incision to a desired width, thereby forming a corneal pocket adapted to subsequently receive the skirt of the artificial cornea; subjecting the resultant patient's cornea to a partial trephination along the central orifice; incising the anterior sac of the crystalline humor along an orifice formed after the partial trephination, and then removing the lenticular nucleus; conducting an anterior vitrectomy for the resultant patient's cornea while sucking the lenticular cortex and posterior sac; sufficiently filling a Viscoat in the eyeball; inserting the artificial cornea into the eyeball under the condition in which sutures are bound to the opposite pieces of the support member of the artificial cornea, respectively; suturing the support member to desired portions of the intrascleral ciliary sulcus, thereby fixing the artificial cornea; inserting the skirt into the corneal pocket, and then suturing the corneal pocket at four positions; cutting the prepared amnion into a circular shape having a desired size, and then detaching the cut amnion from the nylon filter; covering the detached amnion on the artificial cornea; and suturing the amnion in the form of a purse string.

BRIEF DESCRIPTION OF THE DRAWINGS

Other objects and aspects of the invention will be apparent from the following description of embodiments with reference to the accompanying drawings, in which.

DETAILED DESCRIPTION OF THE PREFERRED EMBODIMENTS

Figure 1:
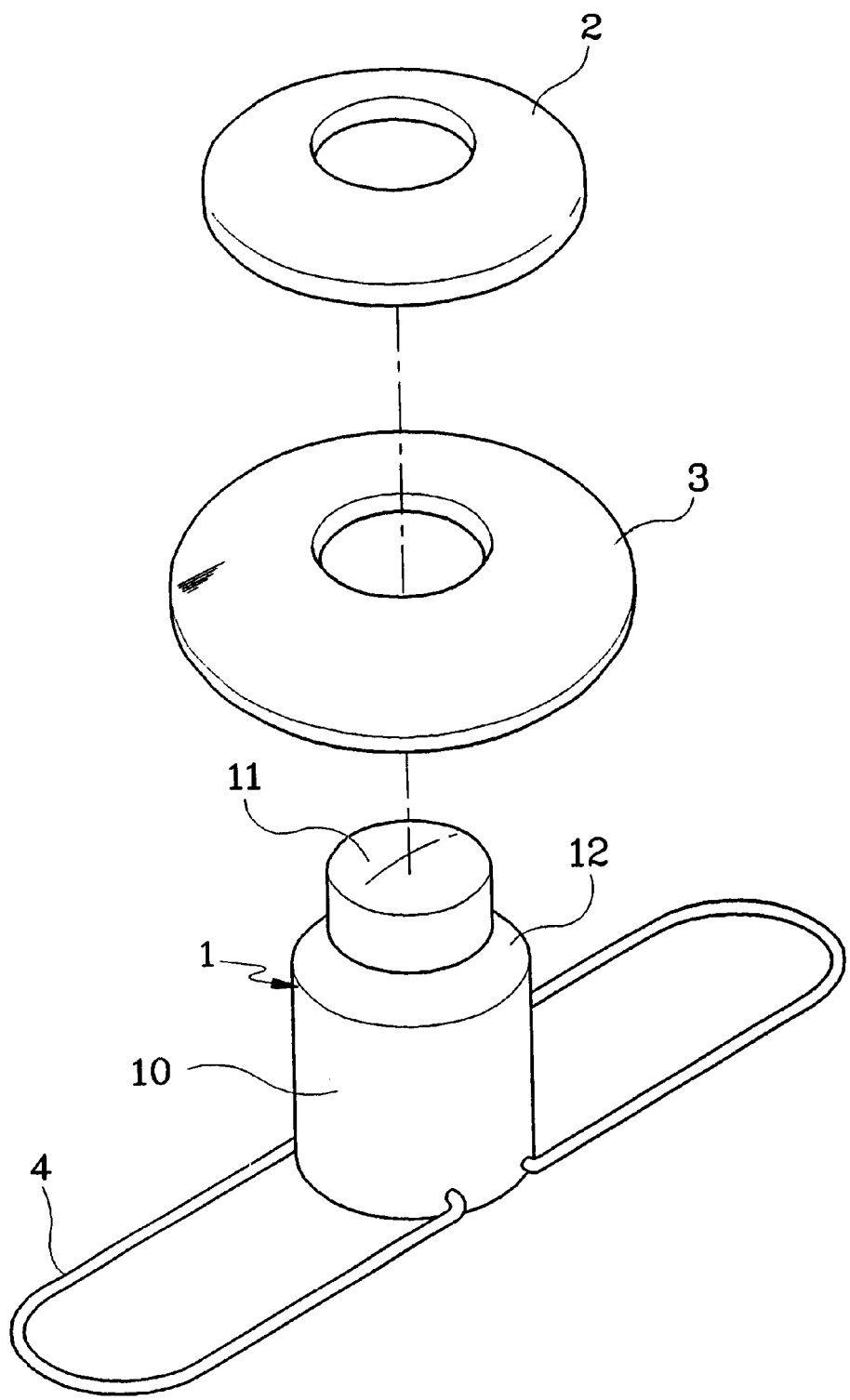
FIG. 1 is a perspective view illustrating an artificial cornea according to the present invention.

Implantation of artificial corneas is required for patients with a severely scarred cornea, to which a transplantation of homologous corneal tissues is impossible. Where such an artificial cornea is grafted only to the cornea of a patient, as in the case of conventional artificial corneas, it may be easily separated from the patient's cornea. To this end, a polyurethane skirt exhibiting a superior biocompatibility is used for a firm graft of the artificial cornea to the patient's cornea in accordance with the present invention. The artificial cornea of the present invention is also configured to be grafted to the inner surface of the healthy sclera.

Conventionally, attempts to prevent the formation of a fibrous membrane at the rear surface of an implant have been made. Such attempts are to provide an artificial cornea with an optic part having an elongated cylindrical shape. In order to promote a stable graft of the artificial cornea to the patient's cornea during an initial reaction period for the recovery of a cut portion of the patient's cornea, a proposal has also been proposed in which the implant is covered with the patient's conjunctival flap. However, many of patients requiring the implantation of an artificial cornea have injured conjunctivas. Furthermore, the patient's conjunctival flap covered on the implant may be shrunken, thereby rather promoting an undesirable melting of the corneal tissue.

To this end, an amnion is covered on the implant in order to promote a stable graft of the artificial cornea to the patient's cornea during an initial reaction period for the recovery of a cut portion of the patient's cornea in accordance with the present invention.

Although not accurately revealed, the amnion, which is a membrane surrounding an fetus in a pregnant woman, it is known as an immunological barrier between the fetus and the pregnant woman.

The amnion consists of an epithelium, a basal membrane, and an interstitium. The basal membrane and interstitium are tissues in which cellular components capable of promoting migration, vegetation, and healing of epithelium cells are rich. Implantation of the amnion to burned skins, ulcerated tissues, and artificial vaginas has been reported. In ophthalmic fields, implantation of the amnion was first made in 1940 for healing of an injured conjunctiva.

Implantation of a human amnion to an experimental burned corneal model of a rabbit has also been reported. However, its success is very limited. In accordance with the present invention, an amnion is covered on the implant not only to promote a stable graft of the artificial cornea to the patient's cornea during an initial reaction period for the recovery of a cut portion of the patient's cornea, but also to obtain a cut cornea portion recovering effect expected by the cellular components of its basal membrane.

In accordance with the present invention, the crystalline humor and vitreous humor are removed in order to suppress complications occurring in the implantation of an artificial cornea, for example, the formation of a fibrous membrane at the rear surface of an implant. By virtue of the removal of the crystalline humor and vitreous humor, the contact area of the artificial cornea with the intraocular tissues is reduced. In accordance with the present invention, an anticoagulant such as heparin is also mixed with a perfusate used.

In order to reduce a melting of tissues around the artificial cornea, a local application or subconjunctival injection of steroid is also carried out in accordance with the present invention. In order to avoid intraocular inflammation, antibiotic is always used before and after the implant operation.

Now, the present invention will be described in detail in conjunction with preferred embodiments, along with the annexed drawings.

Figure 2:
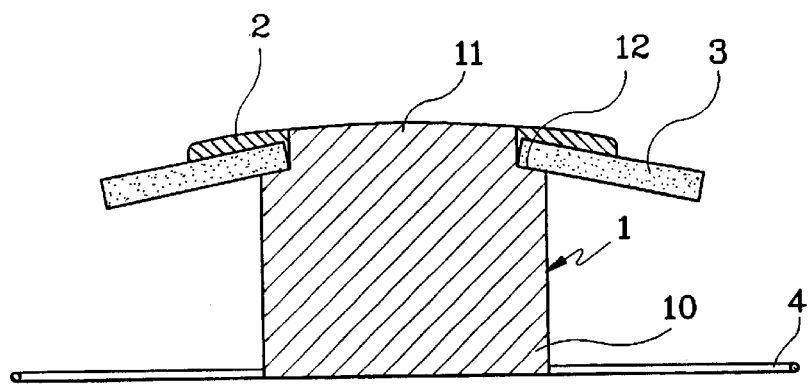
FIG. 2 is a sectional view illustrating the artificial cornea shown in FIG. 1.

FIG. 1 is a perspective view illustrating an artificial cornea according to the present invention. FIG. 2 is a sectional view illustrating the artificial cornea shown in FIG. 1. In addition, FIG. 3 is a sectional view illustrating the condition in which the artificial cornea of the present invention is implanted to an eyeball.

Figure 3:
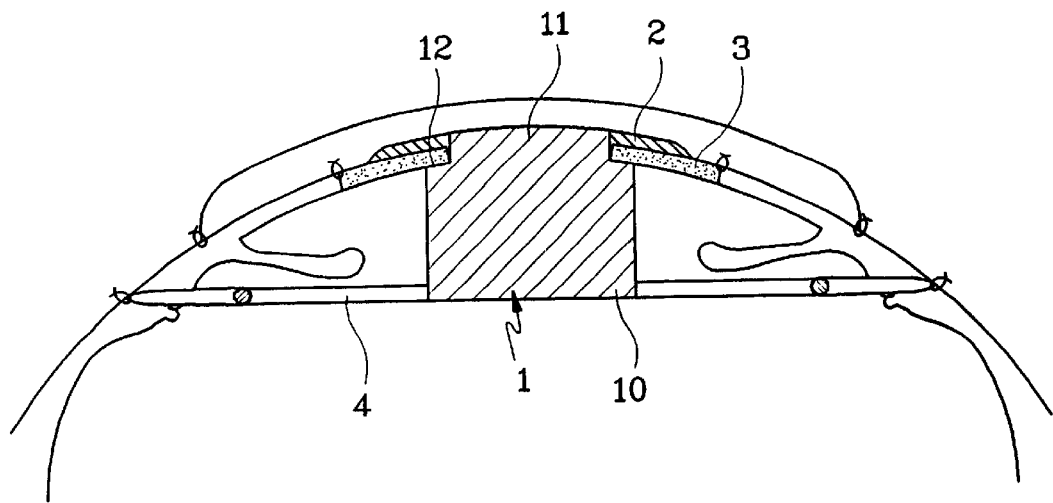
FIG. 3 is a sectional view illustrating the condition in which the artificial cornea of the present invention is implanted to an eyeball.

Referring to FIGS. 1 to 3, the artificial cornea of the present invention includes an artificial cornea body 1, and a anterior flange 2 fitted around the upper portion of the cornea body 1. A skirt 3 is also fitted around the upper portion of the cornea body 1 beneath the anterior flange 2. The anterior flange 2 is coupled to the skirt 3. The cornea body 1 has a cylindrical portion 10 at the lower portion thereof, and an optical portion 11 at the upper portion thereof. The optical portion 11 has a diameter less than that of the cylindrical portion 10 in such a fashion that a step 12 is defined at the lower end of the optical portion 11. A support member 4 is provided at the lower end of the cylindrical portion 10 to support the artificial cornea.

The step 12 has an annular surface inclined in such a fashion that its level is gradually reduced in an outward radial direction. By virtue of such an annular surface of the step 12, the skirt 3 has a curved shape in a state in which it is seated on the annular surface of the step 12.

The anterior flange 2 also has a curved shape having a curvature corresponding to that of the patient's cornea, to be implanted with the artificial cornea, so that it covers the anterior surface of the patient's cornea.

The cornea body 1 is made of a transparent polymethylmethacrylate (PMMA). The skirt 3 is made of porus polyurethane sheet, polypropylene cloth or non-woven, or polyethylene terephthalate cloth or non-woven to have a porous structure with pores having a diameter of 40 m. The skirt 3 also has a thickness of 0.4 mm. The anterior flange 2 is made of fluorosilicon (RGP) exhibiting a high oxygen permeability.

The bonding between the anterior flange 2 and the optical portion 11 and between the skirt 3 and the cylindrical portion 10 is achieved using an n-butyl 2-cyanoacrylate resin which may be Histoacryl as provided by B. Braun, Melsugen AG, Germany. The support member 4 is attached to the cylindrical portion 10 in accordance with an ultrasonic bonding method in which heat is instantaneously generated by ultrasonic waves.

The anterior flange 2 has a diameter of 6 mm, and a thickness of 0.2 mm. The cylindrical portion 10 has a diameter of 4 mm, and a length of 3.5 mm. The skirt 3, which is attached to the rear surface of the anterior flange 2, has an annular structure having an inner diameter of 6 mm, an outer diameter of 9 mm, and a width of 3.0 mm. The support member 4, which is attached to the lower end of the cylindrical portion 10, includes a pair of U-shaped pieces respectively attached to the cylindrical portion 10 at opposite sides of the cylindrical portion 10. The support member 4 has a length of 11 mm in a state in which its U-shaped pieces are attached to the cylindrical portion 10.

All parts of the artificial cornea are disinfected using ethylene oxide gas.

Now, a procedure for implanting the artificial cornea to the patient's cornea in accordance with the present invention will be described in detail.

Preparation of Amnion

A placenta was first obtained from a pregnant woman subjected to a Caesarian operation. The obtained placenta was then cleaned in a laminar flow hood using a physiological salt solution. Thereafter, the amnion of the placenta was peeled off from the chorion. The peel-off of the amnion was easily carried out using a forceps in such a fashion that the forceps was inserted into a space defined between the chorion and the amnion.

The amnion was attached to a nylon membrane filter in a spread state in such a fashion that its epithelium was upwardly exposed. The resultant structure was then cleaned three times using a physiological salt solution mixed with 8 ul/cc of gentamicin and 20 ul/cc of cefamezine.

The cleaned structure consisting of the amnion and nylon membrane filter was then cut into a sample having a size of 2 cm×2 cm. Subsequently, the sample was dipped in a solution consisting of minimum essential media and glycerol mixed together in the same amount, and then stored in a frozen state in a freezer while being maintained at a temperature of −70° C.

Upon the implantation of an artificial cornea, the sample was thawed at room temperature, and then dipped in a physiological salt solution mixed with 8 ul/cc of gentamicin and 20 ul/cc of cefamezine for 30 minutes. The resultant sample was then implanted on the artificial cornea implanted.

Preparation of Operation 24 healthy white domestic rabbits having a weight of 2 to 3 kg and free of eye diseases were used as experimental animals to be operated on. The operation was conducted to the right eye of each rabbit. An eyewash containing 0.3% gentamicin was applied to the right eye of the rabbit at intervals of 3 hours for a period of time from one day before the operation to the operation day in order to reduce a generation of intraocular inflammation after the operation. For a mydriasis, 10% phenylneephrine and 1% tropicamide were applied three times to the right eye of the rabbit at intervals of 5 minutes. After the mydriasis, 30 mg of ketamine per kg of the rabbit's weight and 4 mg of xylazine per kg of the rabbit's weight were intravenously injected into the femur of the rabbit, thereby causing the rabbit to be generally anesthetized. When the anesthesia was released, xylazine was additionally injected.

Operation Procedure

The cornea of the sample was first subjected to a 360 conjunctival incision. A Flieringa fixation ring was sutured at four positions to the sclera exposed through the incised conjunctiva, using a 6-0 black silk suture, so that it was fixed to the sclera.

The epithelium of the cornea was then peeled off using a 69-th Beaver blade. Subsequently, a partial trephination was conducted for the resultant cornea using a corneal circular trephine having a diameter of 6 mm. By this partial trephination, a central orifice having a depth corresponding to about ½ to ⅓ of the thickness of the cornea was formed in the cornea. The resultant cornea was then subjected to a 360 intralamellar incision to a width of 2 mm using the 69-th Beaver blade, so that it was formed with a corneal pocket to subsequently receive the skirt 3 made of polyurethane.

Thereafter, the resultant cornea was subjected again to a partial trephination along the central orifice using a supersharp blade and a pair of corneal scissors. The anterior sac of the crystalline humor was incised along an orifice formed after the partial trephination. In this state, the lenticular nucleus was removed. Subsequently, an anterior vitrectomy was conducted using an Ocutome (manufactured by Alcon Surgical Inc., Fort Worth, Tex., U.S.A.) while sucking the lenticular cortex and posterior sac. The perfusate used at this time was a balanced salt solution (BBS produced by Alcon Surgical Inc., Fort Worth, Tex., U.S.A.) mixed with 20 ul/cc of cefamezine, 8 ul/cc of gentamicin, and 1 ul/cc of heparin. A Viscoat (produced by Alcon Surgical Inc., Fort Worth, Tex., U.S.A.) was then sufficiently filled in the eyeball. In this state, insertion of the artificial cornea into the eyeball was conducted. Prior to the insertion of the artificial cornea, 10-0 polypropylene sutures (produced by Prolene, Ethicon, Edinburgh, U.K.) were bound to the opposite pieces of the support member 4, respectively. After the insertion of the artificial cornea, the support member 4 was sutured to portions of the intrascleral ciliary sulcus respectively corresponding to clock positions of 3 o'clock and 9 o'clock to fix the artificial cornea.

Next, the polyurethane skirt 3 was inserted into the previously formed corneal pocket which was, in turn, sutured at four positions using a 10-0 nylon suture (produced by Alcon surgical Inc., Fort Worth, Tex., U.S.A.).

Thereafter, the amnion, which was stored in a state dipped in a salt solution mixed with an antibiotic, was cut into a size having a diameter of 1.5 cm, and then detached from the nylon filter. The detached amnion was covered on the artificial cornea, and then sutured in the form of a purse string using a 10-0 nylon suture.

During the operation, there was no separation of the artificial cornea from the eyeball.

Subsequently, 20 mg of gentamicin and 20 mg of dexamethasone were subconjunctivally injected. A steroid and antibiotic ointment were applied in the conjunctival sac. Thus, the overall operation was completed. The application of the steroid and antibiotic ointment was conducted every day after the operation. For two weeks after the operation, the subconjuctival injection of gentamicin and dexamethasone was conducted at intervals of three days.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

As apparent from the above description, the present invention provides an inexpensive artificial cornea capable of preventing a separation thereof from an eyeball of the patient during an implant operation thereof while avoiding post-operative complications at the interface between the artificial cornea and the patient's cornea, such as erosive tissue necrosis (melting), leakage of aqueous humor, infection, extrusion of the implant, and intraocular inflammation. The present invention also provides an effective implantation method for the artificial cornea.

What is claimed is:

1. An artificial cornea comprising:
    an artificial cornea body having, at a lower portion thereof, a cylindrical portion adapted to be arranged in the interior of a patient's eyeball, and, at an upper portion thereof, an optical portion adapted to be exposed through an anterior portion of the patient's eyeball, the optical portion having a diameter less than that of the cylindrical portion to define a step at a lower end thereof;
    a skirt fitted around the optical portion of the cornea body and seated on the step;
    an anterior flange coupled to an upper surface of the skirt; and
    a support member attached to a lower end of the cylindrical portion and adapted to support the artificial cornea body.

2. The artificial cornea according to claim 1, wherein:
    the anterior flange has a diameter of 6 mm and a thickness of 0.2 mm;
    the cylindrical portion of the cornea body has a diameter of 4 mm and a length of 3.5 mm;
    the skirt has an annular structure having an inner diameter of 6 mm, an outer diameter of 9 mm, and a width of 3.0 mm; and
    the support member comprises a pair of U-shaped pieces respectively attached to the cylindrical portion of the cornea body at opposite sides of the cylindrical portion and has a length of 11 mm in a state in which the U-shaped pieces are attached to the cylindrical portion.

3. A method for implanting the artificial cornea according to claim 1 or 2 to a cornea of a patient's eye, comprising the steps of:
    preparing a human amnion, and maintaining the prepared human amnion in an antibiotic state;
    subjecting the patient's cornea to a 360 conjunctival incision;
    suturing a Flieringa fixation ring at four positions to the sclera exposed through the incised conjunctiva, thereby fixing the Flieringa fixation ring to the sclera;
    peeling off the epithelium of the patient's cornea;
    conducting a partial trephination for the resultant patient's cornea, thereby forming, in the patient's cornea, a central orifice having a depth corresponding to about ½ to ⅓ of the thickness of the patient's cornea;
    subjecting the resultant patient's cornea to a 360 intralamellar incision to a desired width, thereby forming a corneal pocket adapted to subsequently receive the skirt of the artificial cornea;
    subjecting the resultant patient's cornea to a partial trephination along the central orifice;
    incising the anterior sac of the crystalline humor along an orifice formed after the partial trephination, and then removing the lenticular nucleus;
    conducting an anterior vitrectomy for the resultant patient's cornea while sucking the lenticular cortex and posterior sac;
    sufficiently filling a Viscoat in the eyeball;
    inserting the artificial cornea into the eyeball under the condition in which sutures are bound to the opposite pieces of the support member of the artificial cornea, respectively;
    suturing the support member to desired portions of the intrascleral ciliary sulcus, thereby fixing the artificial cornea;
    inserting the skirt into the corneal pocket, and then suturing the corneal pocket at four positions;
    cutting the prepared amnion into a circular shape, and then detaching the cut amnion from the nylon filter;
    covering the detached amnion on the artificial cornea; and
    suturing the amnion in the form of a purse string.

* * * * *